United States Patent [19]

Hohenschutz et al.

[11] Patent Number: 5,206,433
[45] Date of Patent: Apr. 27, 1993

[54] PREPARATION OF FORMIC ACID

[75] Inventors: Heinz Hohenschutz, Mannheim; Johannes E. Schmidt, Ludwigshafen; Hans Kiefer, Wachenheim, all of Fed. Rep. of Germany

[73] Assignee: BASF Aktiengesellschaft, Ludwigshafen, Fed. Rep. of Germany

[21] Appl. No.: 732,265

[22] Filed: May 9, 1985

[30] Foreign Application Priority Data

May 14, 1984 [DE] Fed. Rep. of Germany ....... 3417790

[51] Int. Cl.$^5$ .......................... C07C 51/44; B01D 3/40
[52] U.S. Cl. ...................... 562/609; 203/15; 203/58
[58] Field of Search .................... 562/609; 203/15, 58; 204/59

[56] References Cited

U.S. PATENT DOCUMENTS

| 4,076,594 | 2/1978 | Buelow et al. | 203/15 |
| 4,218,568 | 8/1980 | Hohenschutz et al. | 562/609 |
| 4,262,140 | 4/1981 | Bott et al. | 562/609 |
| 4,326,073 | 4/1982 | Wolf et al. | 562/609 |

FOREIGN PATENT DOCUMENTS

| 0001432 | 4/1979 | European Pat. Off. . |
| 0012321 | 4/1979 | European Pat. Off. . |
| 2545658 | 4/1977 | Fed. Rep. of Germany . |
| 2545730 | 4/1977 | Fed. Rep. of Germany . |
| 0017866 | 4/1980 | Fed. Rep. of Germany . |
| 1554172 | 10/1979 | United Kingdom . |

OTHER PUBLICATIONS

Migrdichian, V. Organic Synthesis, vol. 1 Reinhold Publishing Corp., N.Y., p. 377 (1957).
Grant, J., Hackh's Chemical Dictionary, 4th ed., McGraw-Hill Book Co., 1969, pp. 34-35.

Primary Examiner—Arthur C. Prescott
Attorney, Agent, or Firm—John H. Shurtleff

[57] ABSTRACT

Anhydrous or substantially anhydrous formic acid is prepared by hydrolyzing methyl formate in the presence of a formamide and then obtaining the formic acid from the hydrolysis mixture by distillation, by a method in which the hydrolysis is carried out in the presence of 0.5–3 moles, per mole of methyl formate, of a water-soluble formamide of the general formula I

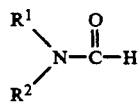

where $R^1$ and $R^2$ are each alkyl or together form an alkylene group, giving a 5-membered to 7-membered ring, with the proviso that the sum of the carbon atoms in $R^1$ and $R^2$ is 5 or 6 and, in the case of an alkylene group, a carbon atom which is not directly bonded to the N atom can be replaced by an oxygen atom.

10 Claims, No Drawings

PREPARATION OF FORMIC ACID

The present invention relates to a novel process for the preparation of formic acid by hydrolyzing methyl formate and then obtaining an anhydrous or substantially anhydrous acid by separating the hydrolysis mixture by distillation.

This basic process is well known but is unsatisfactory because the equilibrium in the hydrolysis

$$H-CO-O-CH_3 + H_2O \rightleftharpoons H-COOH + CH_3OH$$

is established only very slowly and there are difficulties in isolating the formic acid from the aqueous hydrolysis mixture in an anhydrous or substantially anhydrous form.

The solution to these problems forms the subject of a large number of investigations; however, these can be regarded as having met with success, or qualified success, only in the case of special technical embodiments of the process.

According to European Patent 00 01 432, the hydrolysis is carried out in the presence of tertiary nitrogen bases which, like certain imidazole derivatives, have a pKA of 4–9. In this procedure the formic acid is substantially removed from the equilibrium by adduct formation with the base; while on the one hand a high degree of hydrolysis can be achieved, on the other hand the hydrolysis takes place substantially more slowly than in the absence of the base. Furthermore, although the water can readily be separated off completely from the salt-like adduct, cleavage of the adduct for recovery of the acid by distillation requires either such high temperatures that the formic acid undergoes marked decomposition during the procedure, or an uneconomically large reduction in the pressure.

The problem of obtaining the anhydrous acid from the hydrolysis mixture is solved in an outstanding manner by the process of German Laid-Open Application DOS 2,545,658, in which water-insoluble formamides, in particular di-n-butylformamide, serve as extracting agents. In this case, too, an adduct is formed from the formamide and the acid, but the acid can be conveniently distilled off from the adduct without undergoing marked decomposition.

European Patents 0,012,321 and 0,017,866 relate to continuous embodiments of this basic process.

The first-mentioned patent relates to a procedure for carrying out the hydrolysis in the middle section of a distillation column, the lower region of which contains one of the water-insoluble formamides which binds the resulting acid and allows it to pass, in the form of a relatively high-boiling adduct, into the lower section of the column. The bottom fraction obtained in this manner is then separated into acid and formamide in a downstream distillation column, after which the formamide is recycled to the lower region of the hydrolysis section of the column.

The process of European Patent 0,017,866 is essentially based on the recovery of the formic acid from the hydrolysis mixture with the aid of the water-insoluble formamides by the liquid-liquid extraction method, and is accordingly technically designed along these lines. In a particular embodiment of this process, the presence of water-insoluble formamides during the hydrolysis is recommended. Although, owing to adduct formation, this has a favorable effect on the degree of hydrolysis, it is disadvantageous in terms of process engineering in that a two-phase bottom fraction consisting of aqueous formic acid on the one hand and formamide/formic acid on the other hand is obtained when the excess methyl formate and the methanol are separated off from the hydrolysis mixture by distillation; this bottom fraction would have to be separated beforehand, since otherwise it would interfere with the smooth course of the continuous liquid-liquid extraction. It has therefore proven more advantageous to promote the hydrolysis not by means of the water-insoluble formamides but by a large excess of water, especially since no water need be evaporated in the entire process, and even a large excess has a virtually negligible effect in terms of the energy consumption.

However great the overall advantages of the process of European Patent 0,017,866, it is of limited use in that it requires very expensive apparatus and, because of the high capital costs, is economical only above a certain production capacity, which depends on the particular economic circumstances.

Finally, German Laid-Open Application DOS 2,545,730 discloses that aqueous formic acid can be subjected to extractive distillation with N-formylmorpholine and anhydrous acid, or acid having a low water content, can be distilled off, respectively, from the resulting anhydrous bottom fraction or the bottom fraction having a low water content.

It is an object of the present invention to provide a novel process for the preparation of anhydrous or substantially anhydrous formic acid, which process is an industrial and economical alternative to the process of European Patent 0,017,866, in particular for fairly small production capacities.

We have found that this object is achieved by a novel process for the preparation of anhydrous or substantially anhydrous formic acid by hydrolyzing methyl formate in the presence of a formamide and then obtaining the formic acid from the hydrolysis mixture by distillation, wherein the hydrolysis is carried out in the presence of 0.5–3 moles, per mole of methyl formate, of a water-soluble formamide of the general formula I

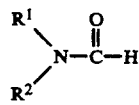

where $R^1$ and $R^2$ are each alkyl or together form an alkylene group, giving a 5-membered to 7-membered ring, with the proviso that the sum of the carbon atoms in $R^1$ and $R^2$ is 5 or 6, and that, in the case of an alkylene group, a carbon atom which is not directly bonded to the N atom can be replaced by an oxygen atom.

We have furthermore found that the hydrolysis takes place particularly rapidly and with high conversion if it is carried out, in a first stage, in the absence of significant amounts of the formamide I until the equilibrium is established, and, in a second stage, in order to increase the conversion, is effected in the presence of a formamide I in the amounts conforming to the definition and based on the amount of methyl formate initially employed.

Regarding the two functions, ie. promotion of the hydrolysis while adding very little water, and trouble-free recovery of formic acid from the formamide/formic acid adducts by distillation, the formamides I have an unexpected optimum action; furthermore, they do not undergo any undesirable side reactions and therefore remain virtually unchanged in their circulation over long operating periods in the continuous embodiment of the process, this embodiment being particularly important industrially.

Among the formamides I, di-n-propylformamide and N-formylmorpholine are particularly important, but another suitable compound is, for example, N-formylpiperidine.

In general, the molar ratio of I to methyl formate employed is from 0.5:1 to 3:1, preferably from 1:1 to 1.5:1. If the hydrolysis is carried out in two stages according to the preferred embodiment, where the formamide I is preferably present in the first stage only in minor amounts (for example up to 10% of its total amount) if at all, the same molar ratios apply since more importance attaches to the formic acid formed than to the methyl formate still present.

Since the degree of hydrolysis increases markedly until the excess of water reaches about 10 moles per mole of methyl formate (a larger excess does not produce any further significant improvement), it would be advantageous to use such an excess of water if it were not necessary to evaporate it again during the distillation, with high energy consumption. Hence, the economically optimum amounts of water when the formamides I are concomitantly used according to the invention are from about 1 to 2 moles per mole of methyl formate; in the two-stage hydrolysis, the total amount of water or the major part thereof should be introduced into the first reactor.

The hydrolysis temperatures are advantageously from 120° to 140° C. in the single-stage hydrolysis, and from 90° to 110° C. in both reactors in the two-stage procedure. This results in a pressure range of about 5-15 bar.

A hydrolysis catalyst, such as sulfuric acid or p-toluenesulfonic acid, may be present but has no significant advantages since the resulting formic acid, being a strong acid, has an autocatalytic action.

The degree of hydrolysis achievable by the novel process is about 40-45%, the two-stage hydrolysis taking place about twice to four times as fast as the single-stage procedure.

After the hydrolysis, excess methyl formate and methanol are separated off in a conventional manner by distillation and are advantageously recycled to the hydrolysis or to the methyl formate synthesis stage.

This distillation gives, as a bottom product, a mixture of water, formic acid and the formamide I, the acid being in the form of a loose adduct with the amide. The water is distilled off from this fraction in a further column in a conventional manner at a bottom temperature of about 80°-150° C. and under 400-1,000 mbar, and is recycled to the hydrolysis. If the formic acid is not required in pure form but only as a highly concentrated aqueous solution, appropriate amounts of water are left behind.

The bottom product from the last-mentioned distillation stage is then separated in a further distillation step, likewise in a conventional manner, into a top fraction consisting of pure or concentrated formic acid and a bottom fraction consisting of the formamide I, which is recycled to the hydrolysis stage. Advantageously, this distillation is carried out under 50-300 mbar and at a bottom temperature of 120°-170° C.

If a batchwise procedure is employed, the three distillation steps can also be effected one after the other in the same column; in the case of continuous operation, it is also possible to carry out the first two steps in one column, with water being taken off as a sidestream.

EXAMPLE 1

61.8 kg/h of a solution of 60 kg (1 kmol/h) of methyl formate and 1.8 kg of methanol,
18.0 kg/h (1 kmol/h) of water and
129.0 kg/h (about 1 kmol/h) of di-n-propylformamide were continuously introduced into a stirred reactor maintained at an internal temperature of 140° C. and under a pressure of about 8 bar and were reacted with one another during a mean residence time of 3 hours. The reacted mixture, which consisted of 35.4 kg/h of methyl formate,
14.9 kg/h of methanol,
17.9 kg/h of formic acid,
11.0 kg/h of water and
129.0 kg/h of di-n-propylformamide, was let down and introduced at the 12th tray (counted from below) of a bubble tray column having 35 trays, and fractionally distilled continuously under atmospheric pressure. At a reflux ratio of 1, this procedure gave:
35.6 kg/h of a mixture of 34.5 kg of methylformate and 1.1 kg of methanol as a top fraction, which was recycled to the hydrolysis reactor,
14.7 kg/h of a liquid sidestream, which was taken off at the 28th tray and consisted of 13.8 kg/h of methanol and 0.9 kg/h of methyl formate, and
157.9 kg/h of a mixture of 17.9 kg/h of formic acid, 11.0 kg/h of water and 129.0 kg/h of di-n-propylformamide as a bottom fraction.

The bottom fraction was substantially dehydrated in a conventional manner in a packed column (15 theoretical plates) under atmospheric pressure, 147.8 kg/h of a mixture of the acid, the formamide and about 0.9 kg of water being obtained as the bottom product.

This mixture was separated, in a second bubble tray column having 20 theoretical plates, under 133 mbar and at a reflux ratio of 1, into
18.8 kg/h of a mixture of 17.9 kg/h of formic acid and 0.9 kg/h of water as a top fraction and
129.0 kg/h of di-n-propylformamide as a bottom fraction, which was recycled to the hydrolysis reactor.

Hence, 18.8 kg/h of 95% strength by weight aqueous formic acid were obtained, corresponding to a yield of 95%. About 5% of the formic acid was lost as a result of decomposition.

EXAMPLE 2

In the manner described in Example 1, but using the same molar amount of N-formylmorpholine instead of di-n-propylformamide, 20.2 kg/h of 95% strength by weight aqueous formic acid were obtained, corresponding to a yield of 95%. The methyl formate conversion in the hydrolysis reactor was 44%.

EXAMPLE 3

In a stirred reactor, 61.8 kg/h (1 kmol/h) of methyl formate (employed as a mixture with 1.8 kg/h of methanol) were hydrolyzed with 18 kg/h (1 kmol/h) of water at 110° C., under about 8 bar and during a mean residence time of 20 minutes, the degree of hydrolysis being 29%.

The hydrolysis mixture was then mixed with 129.0 kg/h (1 kmol/h) of di-n-propylformamide in a second reactor at 110° C. and under about 6 bar, the mean residence time being 1 hour and the degree of hydrolysis increasing to 41%.

Working up by a method similar to that described in Example 1 gave 19.9 kg/h of a 95% strength by weight aqueous formic acid, corresponding to a yield of 100%. No decomposition of the formic acid was observed in this procedure.

We claim:

1. In a process for the preparation of anhydrous or substantially anhydrous formic acid by hydrolyzing methyl formate and then obtaining the formic acid from the hydrolysis mixture by distillation, the improvement which comprises:

carrying out the hydrolysis in the presence of 0.5-3 moles, per mole of methyl formate, of a water-soluble formamide of the formula I

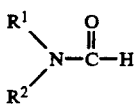

where $R^1$ and $R^2$ are each alkyl or together form an alkylene group, giving a 5-membered to 7-membered ring, with the proviso that the sum of the carbon atoms in $R^1$ and $R^2$ is 5 or 6 and that, in the case of an alkylene group, a carbon atom which is not directly bonded to the N atom can be replaced by an oxygen atom.

2. A process as claimed in claim 1, wherein the hydrolysis is carried out, in a first stage, in the absence of significant amounts of the formamide I until the equilibrium is established, and, in a second stage, in order to increase the conversion, is effected in the presence of a formamide I in the prescribed amounts and based on the amount of methyl formate initially used.

3. A process as claimed in claim 1, wherein the water-soluble formamide I used is di-n-propylformamide.

4. A process as claimed in claim 1, wherein the water-soluble formamide I used is N-3-oxapentamethylene formamide (N-formylmorpholine).

5. A process as claimed in claim 2, wherein the water-soluble formamide I used is di-n-propylformamide.

6. A process as claimed in claim 2, wherein the water-soluble formamide I used is N-3-oxapentamethylene formamide (N-formylmorpholine).

7. A process as claimed in claim 1, wherein the molar ratio of the formamide I to the methyl formate is from 1:1 to 1.5:1.

8. A process as claimed in claim 1, wherein the hydrolysis is carried out at a temperature of from 120° to 140° C. in a single stage.

9. A process as claimed in claim 2, wherein the hydrolysis is carried out at a temperature of from 90° to 110° C. in the two stages.

10. A process as claimed in claim 1, wherein the distillation of the hydrolysis mixture is carried out at a bottom temperature of about 80° to 150° C. and under a pressure of 400 to 1,000 mbar.

* * * * *